United States Patent
Yamamoto et al.

(10) Patent No.: US 10,112,389 B2
(45) Date of Patent: Oct. 30, 2018

(54) INKJET HEAD AND COATING APPARATUS USING SAME

(71) Applicant: Panasonic Intellectual Property Management Co., Ltd., Osaka (JP)

(72) Inventors: Kenichi Yamamoto, Osaka (JP); Kazuki Fukada, Osaka (JP); Tohru Nakagawa, Osaka (JP); Kazunobu Irie, Hyogo (JP); Takeshi Kita, Hyogo (JP); Hidehiro Yoshida, Hyogo (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 15/318,333

(22) PCT Filed: Jun. 24, 2015

(86) PCT No.: PCT/JP2015/003163
§ 371 (c)(1),
(2) Date: Dec. 12, 2016

(87) PCT Pub. No.: WO2015/198594
PCT Pub. Date: Dec. 30, 2015

(65) Prior Publication Data
US 2017/0120587 A1    May 4, 2017

(30) Foreign Application Priority Data

Jun. 27, 2014 (JP) .................................. 2014-132239

(51) Int. Cl.
*B41J 2/14* (2006.01)
*G01N 1/00* (2006.01)
(Continued)

(52) U.S. Cl.
CPC ............. *B41J 2/14145* (2013.01); *B05C 5/00* (2013.01); *B05C 11/10* (2013.01); *B41J 2/14* (2013.01);
(Continued)

(58) Field of Classification Search
CPC .......... B41J 2/14145; B41J 2002/14419; B41J 2002/14467
See application file for complete search history.

(56) References Cited

U.S. PATENT DOCUMENTS 5,896,150 A * 4/1999 Kobayashi ............. B41J 2/1612
347/54
6,045,214 A * 4/2000 Murthy .................. B41J 2/1404
347/47
(Continued)

FOREIGN PATENT DOCUMENTS

JP    2000-017208    1/2000
JP    2003-072104    3/2003
(Continued)

OTHER PUBLICATIONS

International Search Report of PCT application No. PCT/JP2015/003163 dated Sep. 29, 2015.
(Continued)

*Primary Examiner* — Shelby Fidler
(74) *Attorney, Agent, or Firm* — Panasonic IP Management; Kerry S. Culpepper

(57) ABSTRACT

In a common chamber (102) for distributing, to respective pressure chambers (211), an ink supplied from the ink inlet (101), resistant walls (111) are provided in areas that are located ahead and behind of the flow of the ink, i.e., areas around inlets of flow channels (221) that lead to respective pressure chambers (211), and any resistance against the flow of the ink is generated according to the heights of the
(Continued)

resistant walls (111), thereby capturing a solid ingredient (150) included in the ink. In this case, by adjusting the heights of the resistant walls (111) to control capabilities of introducing the solid ingredient (150), it becomes possible to dispense desired amounts of the solid ingredient (150) to the respective pressure chamber (211).

13 Claims, 14 Drawing Sheets

(51) Int. Cl.
   *B05C 5/00*    (2006.01)
   *B05C 11/10*   (2006.01)
   *B41J 2/18*    (2006.01)
   *B41J 2/195*   (2006.01)

(52) U.S. Cl.
   CPC ............ *B41J 2/1404* (2013.01); *B41J 2/1433* (2013.01); *B41J 2/18* (2013.01); *B41J 2/195* (2013.01); *G01N 1/00* (2013.01); *B41J 2002/14419* (2013.01); *B41J 2202/11* (2013.01); *B41J 2202/12* (2013.01)

(56)             References Cited

U.S. PATENT DOCUMENTS

| | | | |
|---|---|---|---|
| 2002/0175980 A1* | 11/2002 | Hashimoto | B41J 2/17513 347/86 |
| 2007/0052763 A1 | 3/2007 | Takatsuka | |
| 2007/0279460 A1 | 12/2007 | Yokoyama et al. | |
| 2008/0018715 A1* | 1/2008 | Wee | B41J 2/055 347/70 |
| 2008/0079759 A1* | 4/2008 | Nagashima | B41J 2/175 347/10 |
| 2009/0009569 A1* | 1/2009 | Sasaki | B41J 2/175 347/85 |
| 2009/0284572 A1 | 11/2009 | Katoh | |
| 2010/0328409 A1 | 12/2010 | Matsufuji et al. | |
| 2011/0164091 A1* | 7/2011 | Takamoto | B41J 2/14274 347/54 |
| 2014/0313261 A1* | 10/2014 | Nagai | B41J 2/1433 347/40 |
| 2014/0354734 A1* | 12/2014 | Pan | B41J 2/175 347/54 |
| 2015/0314601 A1* | 11/2015 | Rivas | B41J 2/1404 347/22 |

FOREIGN PATENT DOCUMENTS

| | | | |
|---|---|---|---|
| JP | 2007-320042 | 12/2007 | |
| JP | 2008-194982 A | 8/2008 | |
| JP | 2011-025663 | 2/2011 | |
| WO | WO 2006103485 A1 * | 10/2006 | ............ B41J 2/1404 |

OTHER PUBLICATIONS

The Extended European Search Report dated Nov. 9, 2017 for the related European Patent Application No. 15811915.6.

\* cited by examiner

INKJET HEAD AND COATING APPARATUS USING SAME

CROSS-REFERENCE TO RELATED APPLICATIONS

This application is a U.S. national stage application of the PCT International Application No. PCT/JP2015/003163 filed on Jun. 24, 2015, which claims the benefit of foreign priority of Japanese patent application 2014-132239 filed on Jun. 27, 2014, the contents all of which are incorporated herein by reference.

TECHNICAL FIELD

The present disclosure relates to an inkjet head, and a coating apparatus using the inkjet head. In particular, the disclosure relates to an inkjet head for an ink including a solid material, and a coating apparatus using the inkjet head.

BACKGROUND

In recent years, as an apparatus for recording characters or images on various recording media, an inkjet printing apparatus has been known. Furthermore, in some apparatuses in the medical field, trace amounts of blood are discharged in an ink-jet system.

When a solid material is discharged together with an ink in the inkjet, stability of discharging such a solid material is low since the solid material sediments inside the inkjet. It is disclosed in JP-A-2000-17208 that the solid material is treated to prevent sedimentation of the solid material.

SUMMARY

However, there are cases where some types of solid materials cannot be treated to prevent sedimentation of the solid materials.

The disclosure was achieved in consideration of the above-mentioned point, and the purpose of the disclosure is to provide an inkjet head that makes it possible to evenly discharge, from multiple nozzles, desired amounts of an ink including a solid material.

In order to solve the above-mentioned problem, the first inkjet head according to the disclosure includes: multiple nozzles that each discharge droplets; multiple pressure chambers that are each connected to the multiple nozzles and that each generate pressures required for discharging of an ink; and a common chamber that supplies the ink to the multiple pressure chambers. The first inkjet head further includes: multiple discrete flow channels that each supply the ink to the respective multiple pressure chambers from the common chamber; and an ink inlet from which the ink is supplied to the common chamber. In addition, resistant walls are provided in respective inlets of the multiple discrete flow channels.

Moreover, the second inkjet head according to the disclosure includes: multiple nozzles that each discharge droplets; multiple pressure chambers that are each connected to the multiple nozzles and that each generate pressures required for discharging of an ink; and a common chamber that supplies the ink to the multiple pressure chambers. The second inkjet head further includes: multiple discrete flow channels that each supply the ink to the respective multiple pressure chambers from the common chamber; and an ink inlet from which the ink is supplied to the common chamber. In addition, heat-generation parts are provided in respective inlets of the multiple discrete flow channels, and an amount of heat generation in at least one of the heat-generation parts differs from the other heat-generation parts.

Furthermore, a coating apparatus using the above inkjet head(s) is used.

As described above, according to the disclosure, an inkjet head that makes it possible to supply any amounts of a solid ingredient included in an ink to multiple pressure chambers can be configured. Accordingly, required amounts of a material can be supplied to targeted nozzles, and usability of the material can be improved. Furthermore, any disposal loss can be reduced.

DESCRIPTION OF EMBODIMENTS

Hereinafter, embodiments of the invention will be described with reference to drawings.

First Embodiment

<Structure>

Figure 1A:
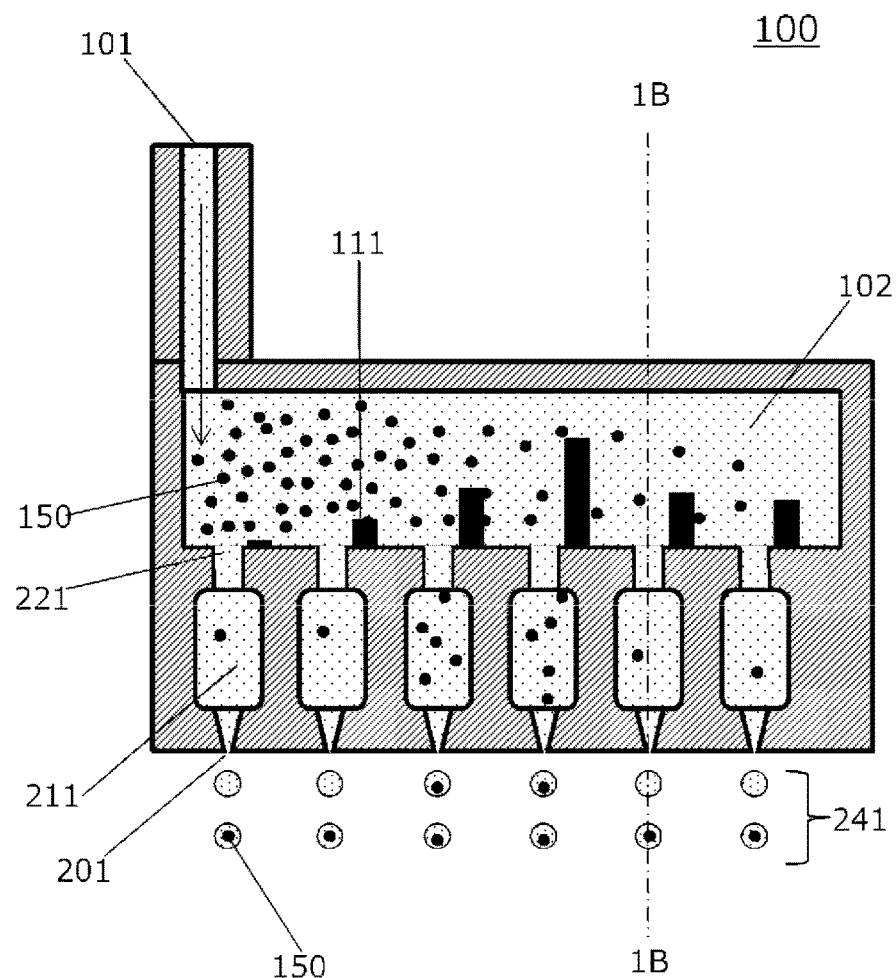
FIG. 1A is a cross-section view that shows a structure of an inkjet head according to a first embodiment of the disclosure.

FIG. 1A is a cross-section view of an inkjet head 100 according to a first embodiment of the disclosure when viewed from the front. The inkjet head 100 includes multiple nozzles 201. Pressure chambers 211 that are each communicated with the respective multiple nozzles 201 are provided in the inkjet head.

Furthermore, an ink inlet 101 is provided in the inkjet head 100, and leads to a common chamber 102. Discrete flow channels 221 that are each communicated with the respective pressure chambers 211 from the common chamber 102 are provided in the inkjet head.

<Drive>

Figure 1B:
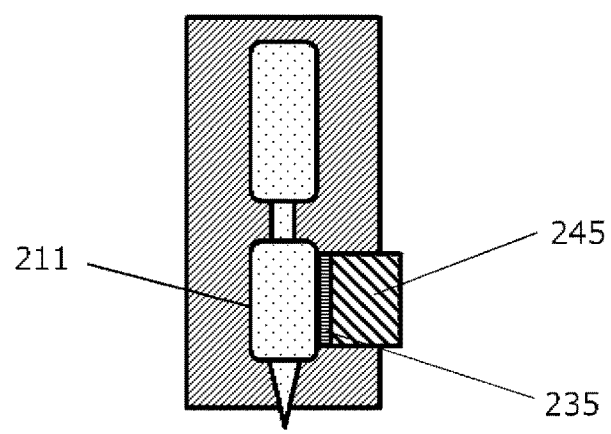
FIG. 1B is a cross-section view that shows the structure of the inkjet head along the line 1B-1B in FIG. 1A.

Next, a mechanism that drives the inkjet head 100 will be described. FIG. 1B is a cross-section view along the line 1B-1B in FIG. 1A. In FIG. 1B, one side surface of the inkjet head 100 is opened, a vibration plate 235 that transmits a pressure to an ink is placed at the opened side of the pressure chamber 211, and a piezoelectric element 245 is further provided on the vibration plate 235. Thus, there is a mechanism in which a displacement of the piezoelectric element 245 is transmitted to the pressure chamber 211 through the vibration plate 235.

In addition, each of the respective pressure chambers 211 has the same pressure-generation mechanism according to the piezoelectric element 245.

<Flow of Ink>

Next, a process leading to discharge of an ink will be described. The ink that has been introduced from the ink inlet 101 is accumulated in the common chamber 102 that serves as a reservoir for dispensing the ink to the respective pressure chambers 211.

The ink filled in the common chamber 102 is caused to flow into pressure chambers 211, which are located downward, through discrete flow channels 221 according to the pressure and the gravity of the ink introduction, and eventually reaches the nozzles 201.

A diameter of each nozzle in the inkjet head 100 is typically about 0.2 mm at a maximum, and never falls in drops due to the surface tension of the ink. The ink is filled inside the inkjet head 100. Due to a pressure generated by each piezoelectric element 245, which is located inside the corresponding pressure chamber 211, the ink filled inside the pressure chamber 211 is delivered to the corresponding nozzle 201 by pressure. The pressure is further transmitted to the nozzle 201, and thus, the ink to which pressure has been applied is discharged to the outside as droplets 241.

A type of the ink used herein is not particularly limited, and can be selected as appropriate according to types of products. Although an ink formed by dissolving a desired ingredient in a water medium is generally used, there are cases in which an organic solvent is used in order to effectively carried out dissolution and dispersion for some types of materials such as dyes and pigments.

Furthermore, in order to improve design properties of the printing surface, inks of so-called metallic materials that include metal oxides such as aluminum and titanium can be used.

Additionally, because of the recent progress of biotechnology, biological inks that include cells of organisms can also be used. These inks make it possible to form patterns of any cells by the inkjet technology, thus forming biological structures. Biological inks include cells, which are solid ingredients, adhesive proteins, etc. Inks formed by dispersing cells in culture media for culturing cells can also be used.

<Resistant Wall 111>

Next, in discrete flow channels 221 inside the common chamber 102, resistant walls 111 are provided in areas (inlets of discrete flow channels 221) that are located ahead and behind (inlets of discrete flow channels 221) of the flow direction of the ink. Due to the presence of the resistant walls 111, effects to impede the flow of the ink inside the common chamber 102, i.e., the flow which is generated during introduction, discharging and filling of the ink, are produced. This resistant walls 111 may be provided not in inlets of the discrete flow channels 221 but between the inlets.

Figure 2:
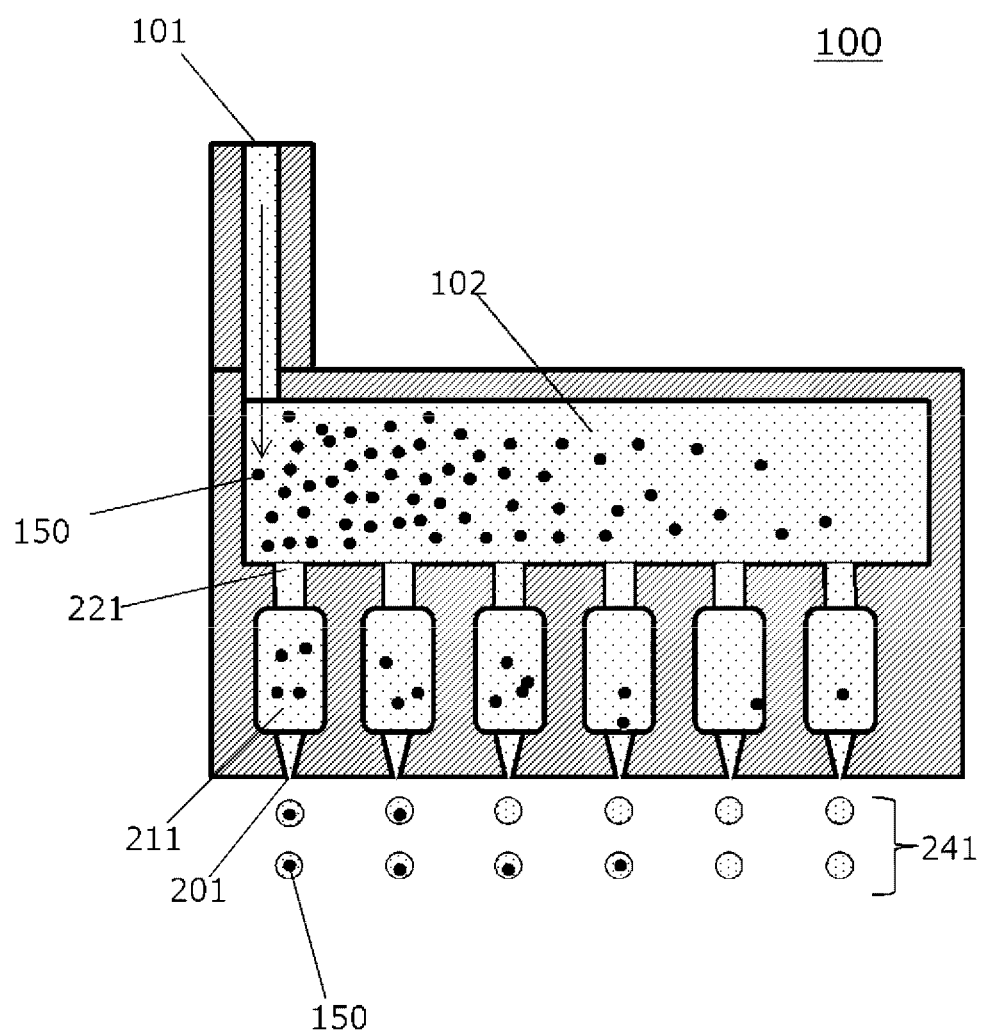
FIG. 2 is a cross-section view that shows a structure of a conventional inkjet head.

Effects of the resistant walls 111 will be described by comparison with a case in which no resistant walls are present. FIG. 2 is a cross-section view of an inkjet head 100, showing a distribution state of a solid ingredient 150 in a case where no resistant walls 111 are present.

In the inkjet head 100, the ink that has been supplied from the ink inlet 101 is filled into the common chamber 102. Then, the ink including a solid ingredient 150 is introduced into each discrete flow channel 221. In this case, if resistant walls 111 are not present as shown in FIG. 2, the ink is successively introduced into the discrete flow channels 221 while flowing above the discrete flow channels 221. Accordingly, the concentration of the solid ingredient 150 included in the ink to be introduced thereto is higher at the upstream of the flow of the ink, and is lower at the downstream.

Therefore, even if amounts of the ink introduced into the respective discrete flow channels 221 are the same, the concentrations of the solid ingredient 150 to be introduced gradually become lower toward the direction from the upstream to the downstream of the flow of the ink. As a result, the amounts of the solid ingredient 150 introduced into the respective discrete flow channels 221 will be more intensively reduced toward the downstream.

Next, when resistant walls 111 shown in FIG. 1A are provided in the common chamber 102, the solid ingredient 150 is prevented from moving by the resistant walls 111, loses speed, and is led to discrete flow channels 221 as a function of filling involved with consumption of the ink. Accordingly, it becomes possible to control an amount of the solid ingredient 150 that is left out of the flow and that is captured, by adjusting the heights of the resistant walls 111. Since the heights of the resistant walls 111 and the probability of capture of the solid ingredient 150 are obtained in such a manner that they are approximately proportional to one another, the amounts of the solid ingredient 150 that are lead to the respective discrete flow channels 221 can be controlled. In this case, a height of a resistant wall 111 has the same meaning as an area of the resistant wall 111.

According to the above structure, a resistance against the flow is generated by resistant walls 111, the solid ingredient can be captured depending on the degree of resistance, and an amount of the solid ingredient 150 that is led to each pressure chamber 211 can actively be controlled.

Figure 1C:
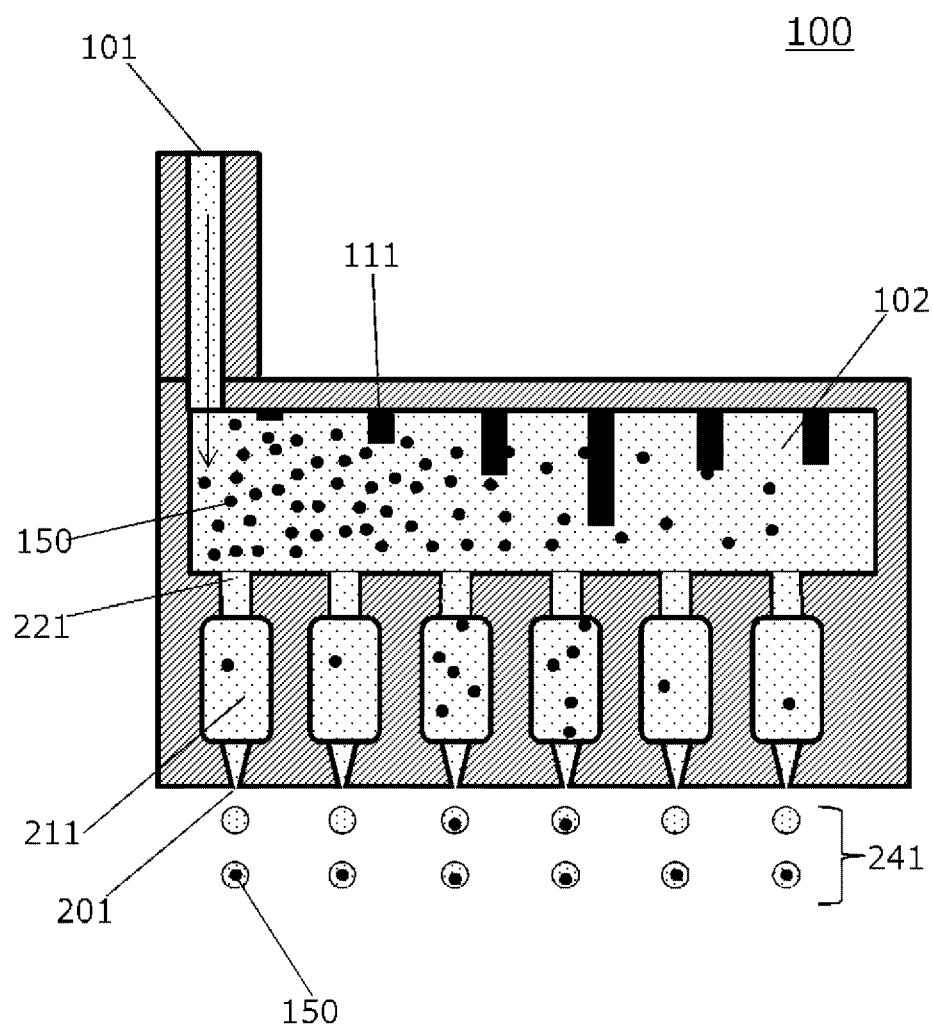
FIG. 1C is a cross-section view that shows a structure of an inkjet head according to the first embodiment.

In addition, as shown in FIG. 1C, resistant walls 111 may be provided on the upper face of the common chamber 102.

<Variation Example of Resistant Wall 111>

Figure 3:
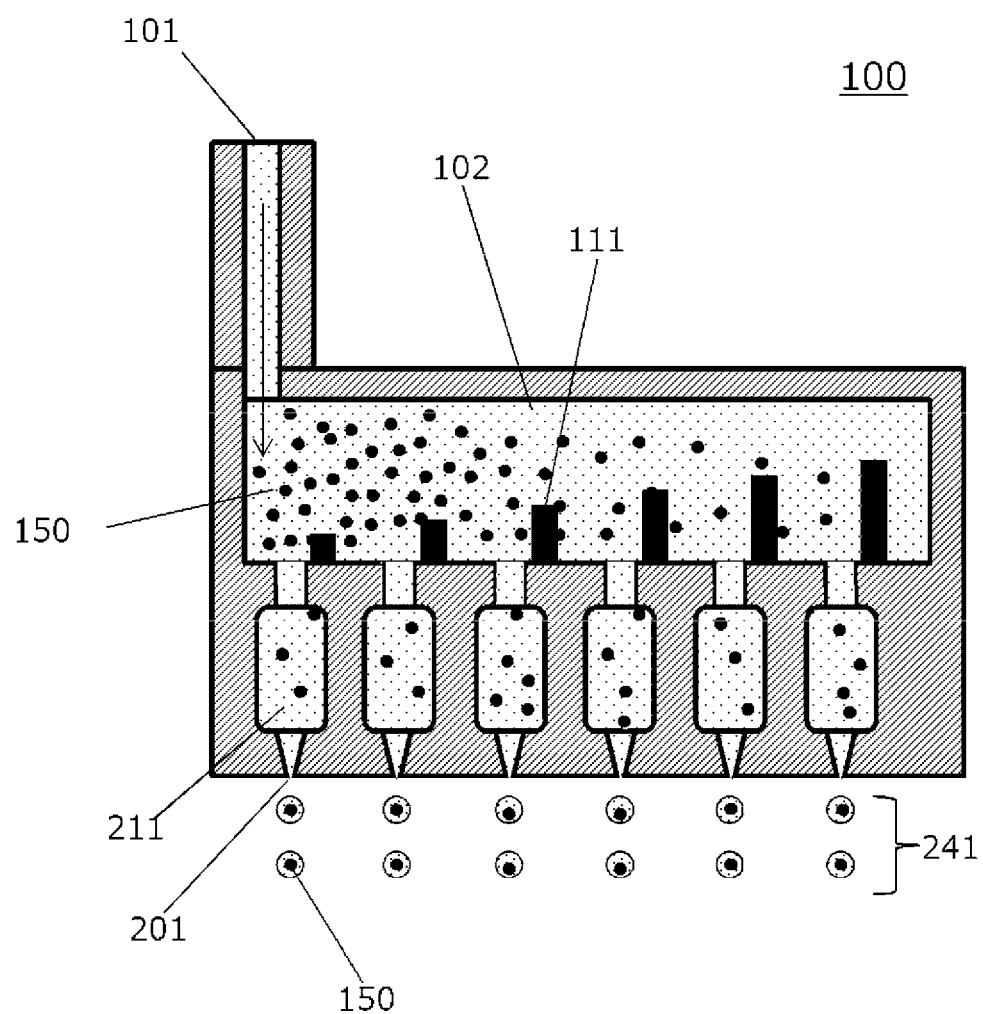
FIG. 3 is a cross-section view that shows another example of a structure of an inkjet head according to the first embodiment of the disclosure.

Furthermore, a variation example of FIG. 1A is shown in FIG. 3. In FIG. 3, heights (or sizes or areas) of resistant walls 111 are changed by location. By designing resistant walls in such a manner that, in the common chamber 102 inside the inkjet head 100, they are lower in height (narrower) at the upstream of the flow, and are higher in height (larger) at the downstream of the flow, the solid ingredient 150 to be captured can equally be distributed.

Specifically, the resistant wall 111 that is located at the most upstream side (the side on which the ink inlet 101 is present) is the lowest in height, and the resistant walls 111 becomes higher in heights toward the downstream. As mentioned above, this means that, with regard to the ink present at the upstream side where a high concentration of solid ingredient 150 is present, the capturing probability is lowered by use of a low-height resistant wall, while, with regard to the ink present at the downstream side where a low concentration of solid ingredient is present, the capturing probability is attempted to improve by use of a high-height resistant wall. Thus, the concentration of the solid ingredient 150, which had typically been biased is evenly distributed. Accordingly, it becomes possible to evenly control the solid ingredient 150 that is actually introduced into the pressure chambers 211, resulting in discharge of the ink.

The resistance against the flow is set to be smaller around the upstream side of the flow direction where a higher concentration of the solid ingredient 150 is present, and the resistance against the flow is set to be larger around the downstream side of the flow direction where a lower concentration of the solid ingredient 150 is present, and this makes it possible to equally distribute the solid ingredient 150 with respect to the multiple pressure chambers 211.

<Evaluation>

Figure 4:
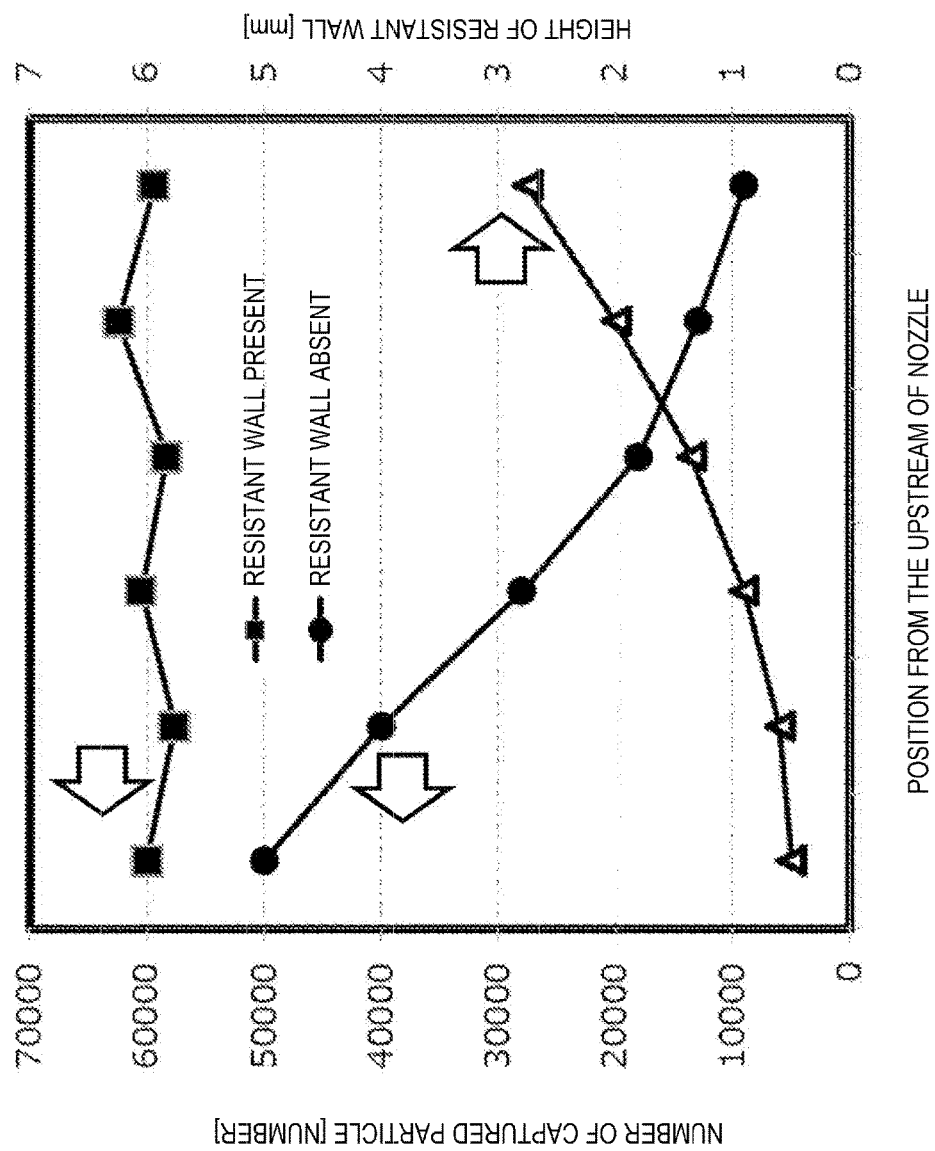
FIG. 4 is a graph that shows the numbers of solid ingredients captured by resistant walls in the inkjet head on each nozzle according to the first embodiment of the disclosure.

FIG. 4 shows a relationship between the capture number of solid ingredient 150 (the number of captured particles) and the heights of resistant walls 111 after the ink is continuously discharged for 10 minutes. FIG. 4 refers to results with regard to the structure in FIG. 3.

Because, as shown in FIG. 4, the concentration of the solid ingredient 150 in the ink is reduced toward the direction from the upstream to the downstream, the capture number of the solid ingredient 150 (the number of captured particles) is decreased in cases where resistant walls 111 are not present. However, by providing resistant walls 111 to improve the capturing probability, the solid ingredient 150 can be evenly captured. Additionally, it is shown that the mean capture number can also be improved.

<Variation Example>

Figure 5A:
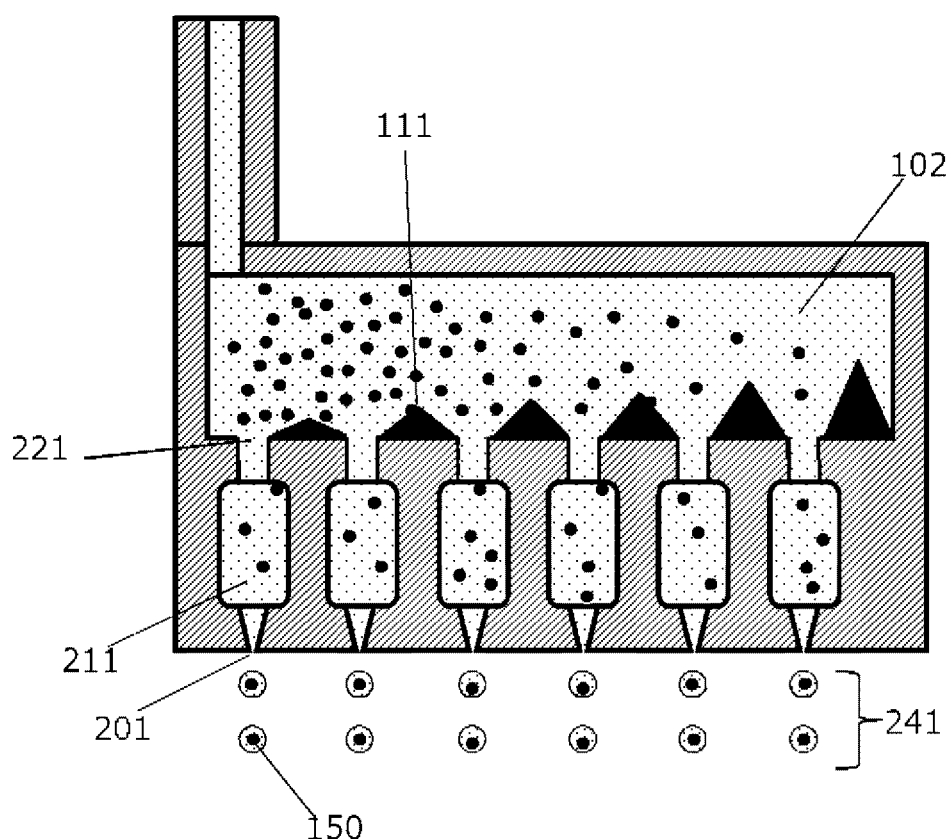
FIG. 5A is a cross-section view that shows still another example of a structure of an inkjet head according to the first embodiment of the disclosure.
Figure 5B:
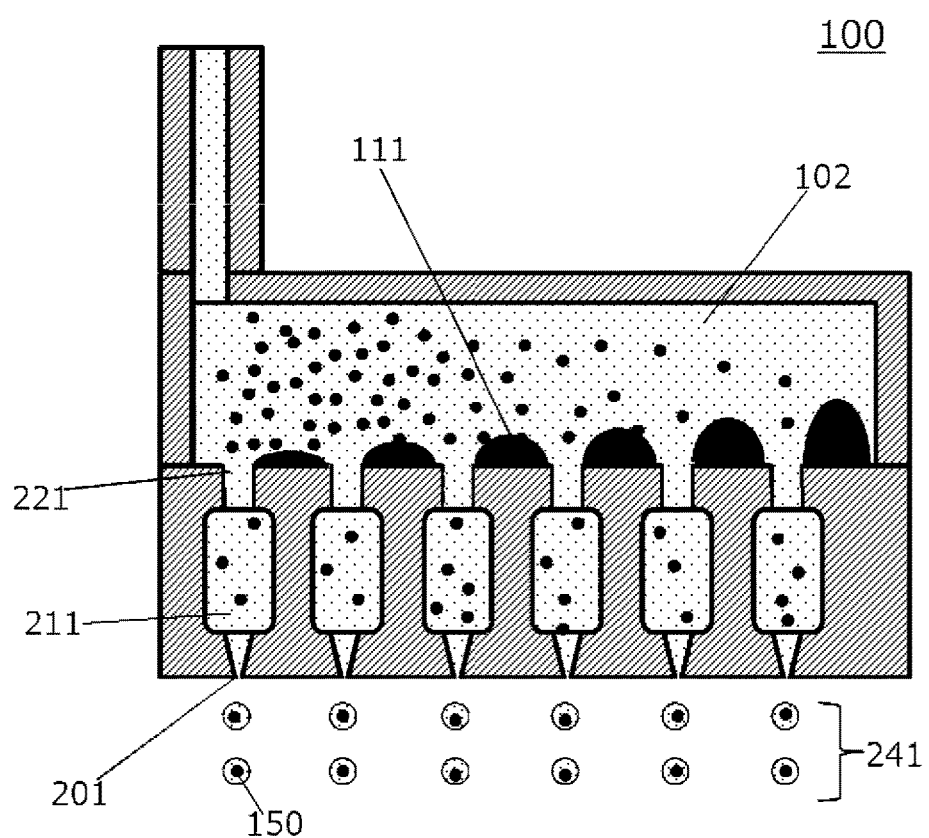
FIG. 5B is a cross-section view that shows even still another example of a structure of an inkjet head according to the first embodiment of the disclosure.

Furthermore, although, in the above description, a rectangular resistant wall 11 is shown by figures, not only such a rectangular shape but also shapes such as a triangle and ellipse as shown in FIGS. 5A and 5B can bring about the same effects as long as the shapes can be voluntarily controlled. Although the above description is made based on the height, it also means increasing the area, i.e. a rate of resistance.

In cases of FIGS. 5A and 5B, resistant walls 111 occupy intermediate areas between discrete flow channels 221, and these variation examples are more preferable.

Second Embodiment

Figure 6A:
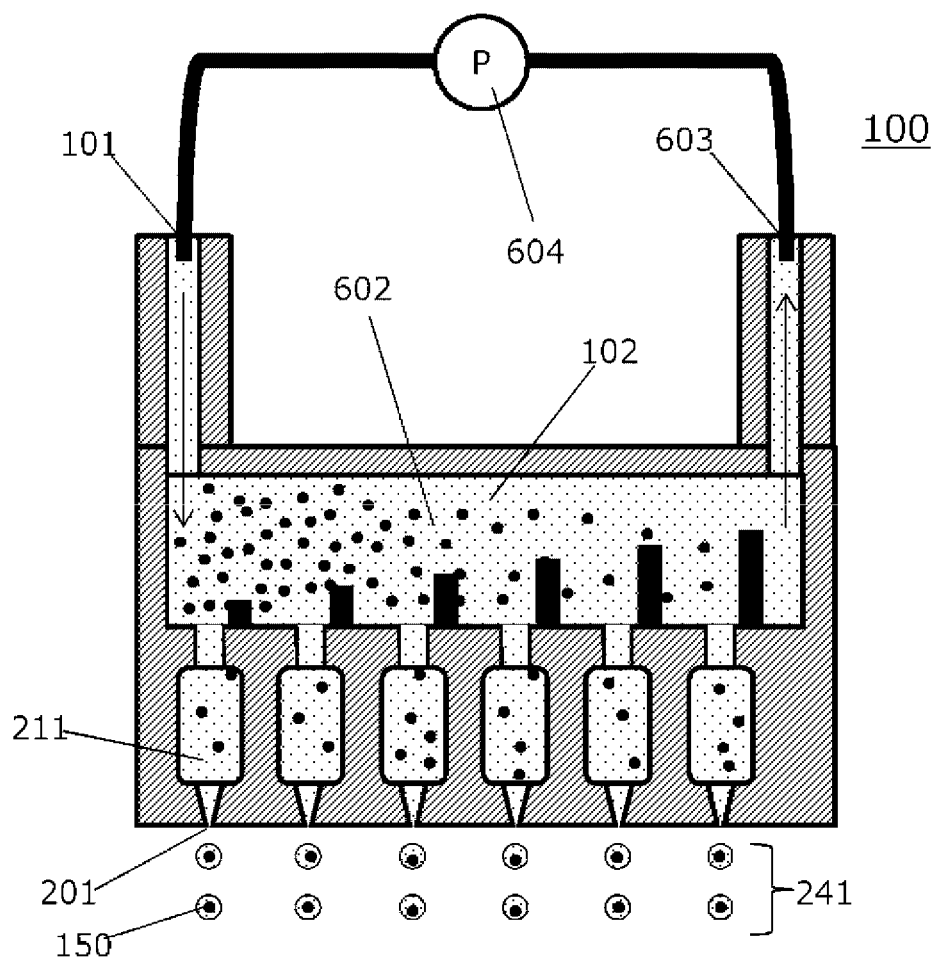
FIG. 6A is a cross-section view that shows another example of a structure of an inkjet head according to a second embodiment of the disclosure.

Although, in the first embodiment, only the flow of the ink from the ink inlet 101 is described, it is also possible to circulate the ink by providing an ink outlet 603. FIG. 6A is a conceptual diagram that shows a shape of a common chamber 102 in a case where such an ink outlet 603 is provided.

In FIG. 6A, an ink inlet 101 and the ink outlet 603 are provided in a common chamber 102 in an inkjet head 100, and an ink that has been retrieved from the ink outlet 603 is again introduced from the ink inlet 101 by an outside pump 604, thereby providing an action of circulation of the ink. By using this action to cause not only the flow of the ink due to filling of the ink based on consumption of the ink, but also compulsory flow of the ink, more suitable distribution of the solid ingredient can be realized.

Figure 6B:
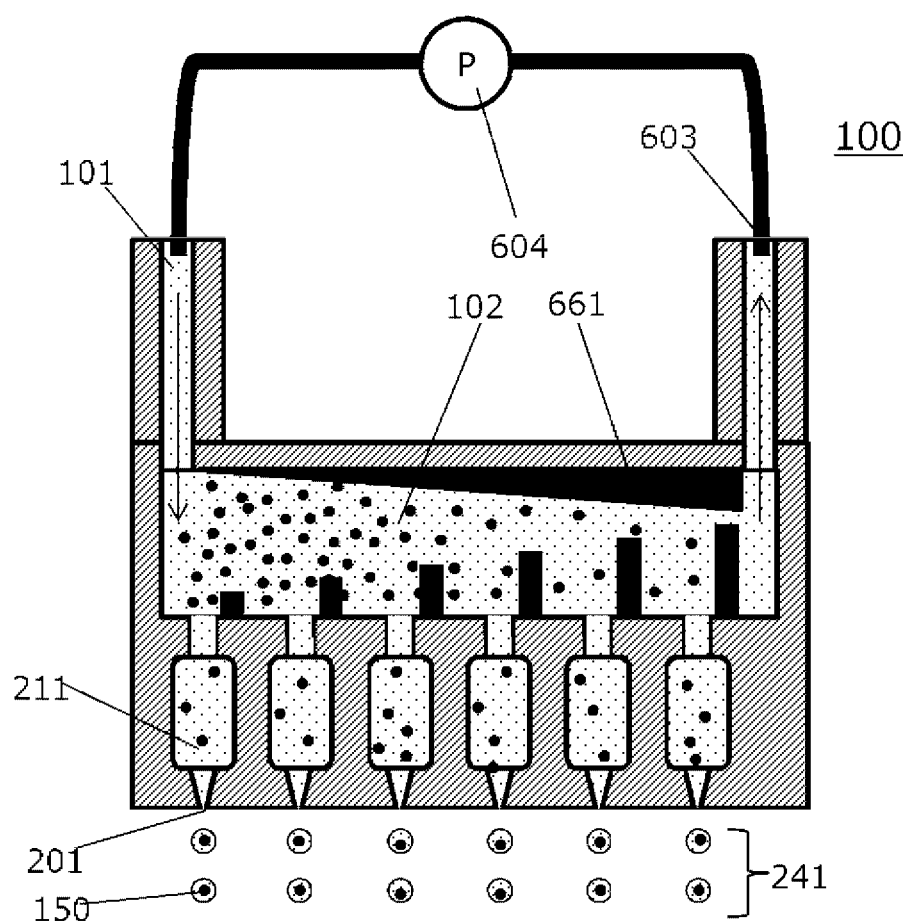
FIG. 6B is a cross-section view that shows another example of a structure of an inkjet head according to the second embodiment of the disclosure.

Furthermore, by enlarging a ceiling part 661 at the side where the ink outlet 603 is present as shown in FIG. 6B, the action of resistant walls is amplified, and thus, it becomes possible to more efficiently distribute the solid ingredient. In this case, to enlarge the ceiling part 661 means to increase its area.

Not only the flow of the ink supply in association with reductions in ink due to the discharge from nozzles but also a more active flow of the ink can be produced, and thus, it becomes possible to enhance effects of the invention. Matters not described in this embodiment are the same as the first embodiment.

Third Embodiment

Figure 7:
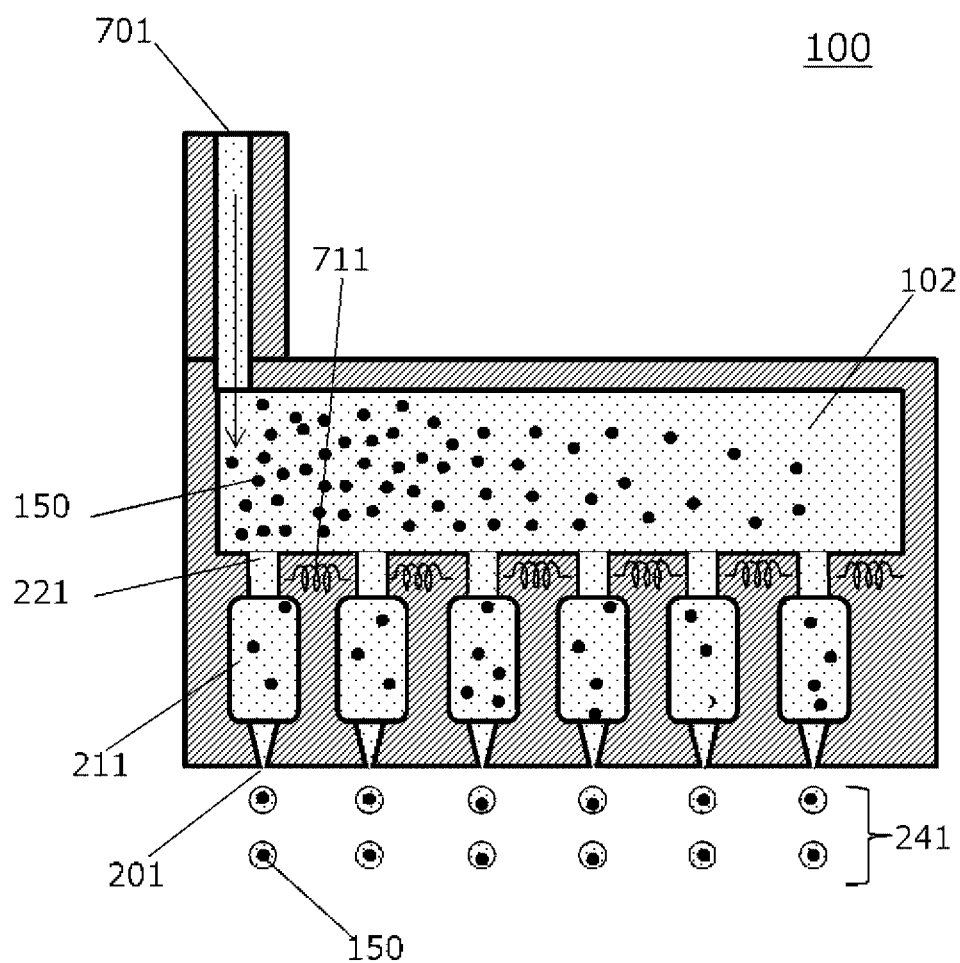
FIG. 7 is a cross-section view that shows a structure of an inkjet head according to the third embodiment of the disclosure.

FIG. 7 is a cross-section view of an inkjet head 100 in a second embodiment of the invention when viewed from the front. The inkjet head 100 has multiple nozzles 201. Pressure chambers 211 that are each communicated with the multiple nozzles 201 are provided in the inkjet head.

Furthermore, an ink inlet 701 is provided in the inkjet head 100, and leads to a common chamber 102. Discrete flow channels 221 that are each communicated with the common chamber 102 and the pressure chambers 211 are provided.

Next, a mechanism that drives the inkjet head 100 will be described.

In addition, a pressure-generation mechanism based on a piezoelectric element 245 is present in common in the respective pressure chambers 211 in FIG. 7.

In this embodiment, in the discrete flow channels 221 inside the common chamber 102, heat-generation parts 711 are provided in areas that are located ahead and behind of the flow direction of the ink.

Due to the presence of the heat-generation parts 711, an action to prevent the flow of the ink inside the common chamber 102, i.e., the flow of the ink that is caused during introduction of the ink and during filling of the ink in association with consumption of the ink caused by discharge of the ink, is produced.

<Heat-Generation Part 711>

Action of heat-generation parts 711 will be described. The heat-generation parts 711 can locally heat the ink present in the vicinity of them, and this makes it possible to produce local upward flows inside the common chamber 102. The upward flows have components that are perpendicular to the flow of the ink inside the common chamber 102, and exhibit actions to impede the ordinary flow of the ink.

The solid ingredient 150 is impeded by the upward flows, thus losing speed, and is led to discrete flow channels 221 as a function of filling involved with consumption of the ink. Accordingly, an amount of the solid ingredient that is left out of the flow and that is thus captured can be controlled by the strength of the upward flows. Since the strength of the upward flows and the probability of capture of the solid ingredient are obtained in such a manner that they are approximately proportional to one another, an amount of the solid ingredient that is led to each of the discrete flow channels 221 can be controlled. The strength of the upward flows can be managed based on the amount of heat generation, and therefore, as a result, by controlling the amount of heat generation, the resulting amount of the solid ingredient can be controlled.

The heat-generation parts 711 may be formed by embedding small-sized heaters into the inkjet head, or thin-film heaters may be formed during production of the inkjet head by way of thin-film forming.

According to the above structure, heat generation by heat-generation parts 711 causes upward flows that serve as resistant flows against the flow of the ink, and thus, the amount of the solid ingredient that is introduced into the pressure chambers is increased depending on the degrees of the resistant flows. According to heat generation by the respective heat-generation parts 711, it becomes possible to actively control amounts of the solid ingredient that are led to the respective pressure chambers.

Figure 8:
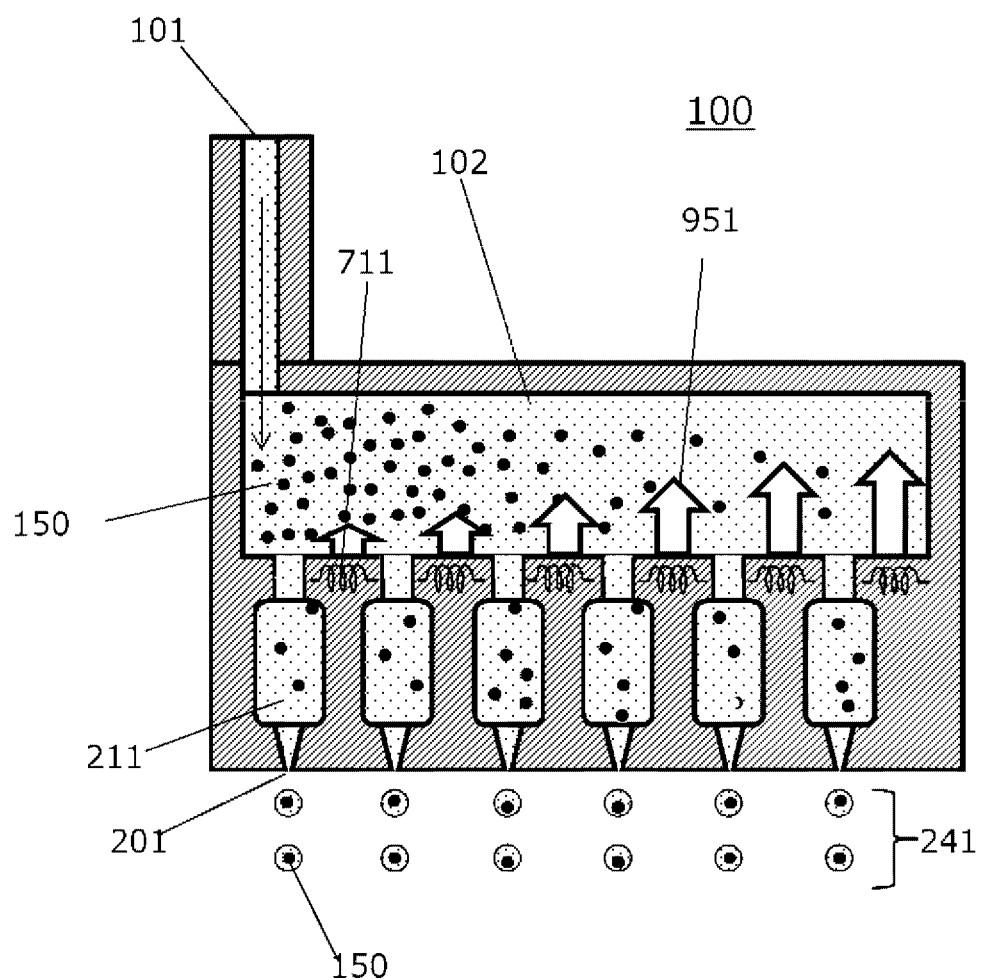
FIG. 8 is a cross-section view that shows the structure and action of the inkjet head according to a third embodiment of the disclosure.

Furthermore, a variation example of FIG. 7 is shown in FIG. 8. In a common chamber 102 inside an inkjet head 100, an amount of heat generation is controlled to be higher at the upstream side of the flow of the ink, and to be lower at the downstream side. This makes it possible to evenly distribute the solid ingredient that is captured by each nozzle.

Specifically, an upward flow 951 (shown by arrows in the figure) is the smallest at the most downstream edge, and gets larger toward the upstream side. The amount of heat generation is produced to realize such conditions.

In other words, as described above, with regard to the ink present around the upstream side where a high concentration of the solid ingredient is present, the upward flow is adjusted to be smaller, thereby decreasing the capturing probability, and, with regard to the ink present around the downstream side where a low concentration of the solid ingredient is present, a strong upward flow is used to improve the capturing probability. This makes it possible to evenly distribute a concentration of the solid ingredient, which had typically been biased. This makes it possible to homogenously control the solid ingredient that is actually introduced to pressure chambers, resulting discharge. Matters not described in this embodiment are the same as the first embodiment 1.

Fourth Embodiment

Figure 9A:
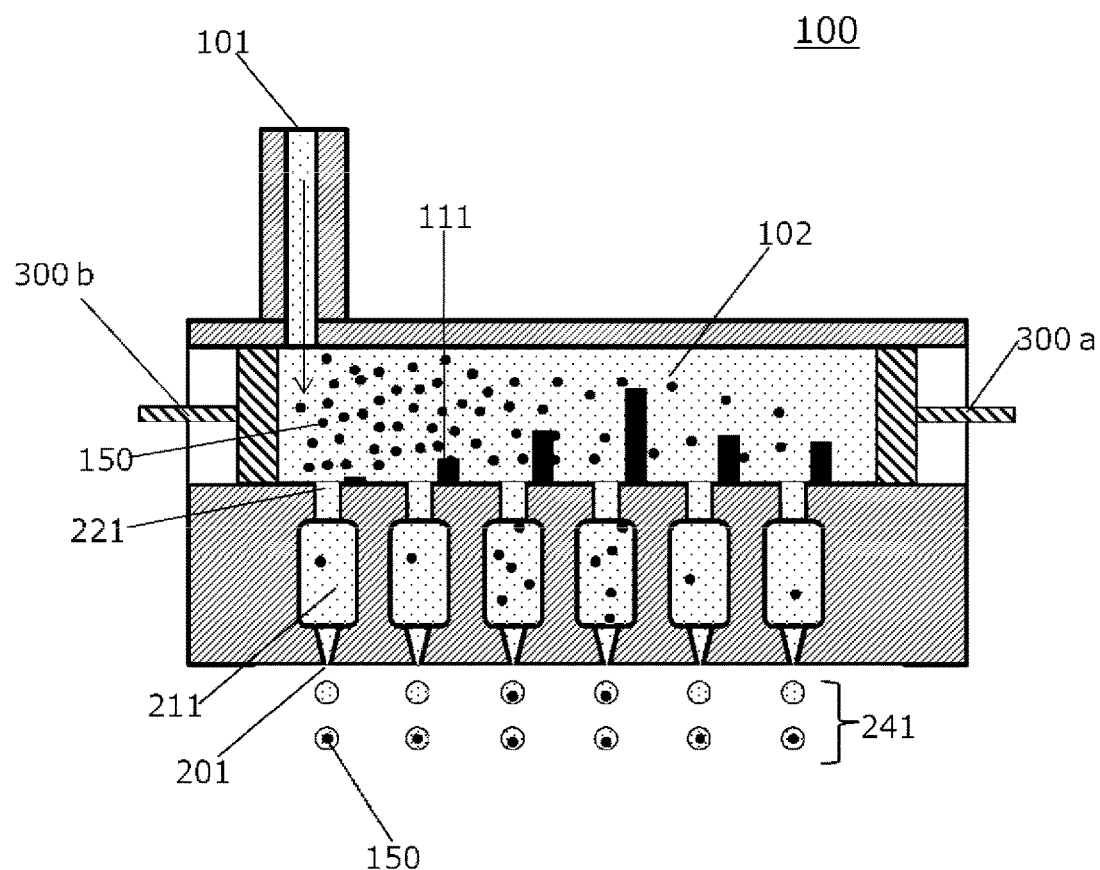
FIG. 9A is a cross-section view that shows a structure of an inkjet head according to a fourth embodiment of the disclosure.
Figure 9B:
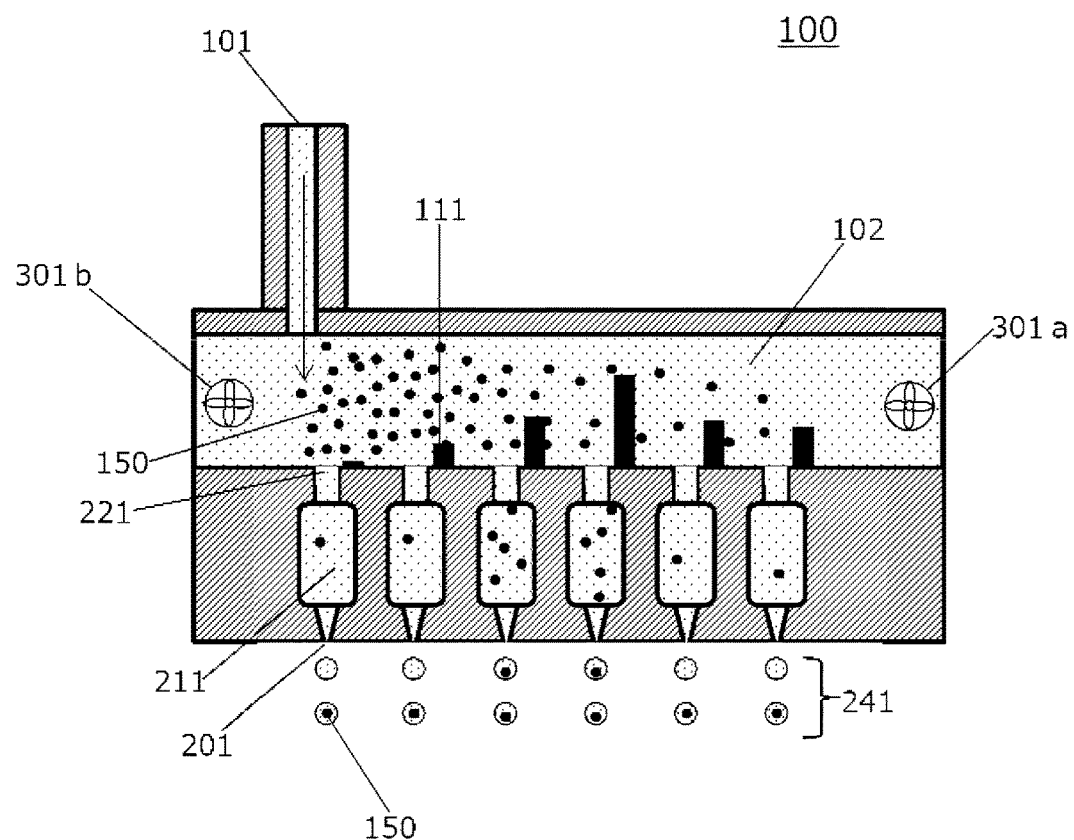
FIG. 9B is a cross-section view that shows a structure of an inkjet head according to the fourth embodiment of the disclosure.

FIGS. 9A and 9B are cross-section views of inkjet heads according to a fourth embodiment of the invention when viewed from the fronts.

In this embodiment, an oscillating mechanism is provided in addition to the structure according to the first embodiment in FIG. 1A. Matters not described in this embodiment are the same as the first embodiment.

In FIG. 9A, pistons 300a and 300b that serve as such an oscillating mechanism are provided in a common chamber 102. The pistons 300a and 300b are provided at both sides of the common chamber 102. The pistons 300a and 300b are synchronized with one another. The pistons 300a and 300b simultaneously move to the left, and simultaneously move to the right. In association with the movements, the ink in the common chamber 102 is oscillated.

In FIG. 9B, blades 301a and 301b that serve as the oscillating mechanism are provided in a common chamber 102. The blades 301a and 301b are provided at both sides of the common chamber 102. The blades 301a and 301b are rotated to thereby stir the ink. Only either one of the blades 301a or 301b may be provided.

According to the oscillating mechanism, the ink inside the common chamber 102 can be stirred, and the solid ingredient 150 can be homogenously stirred in the common chamber 102. As a result, the solid ingredient 150 penetrates homogenously into the respective pressure chambers 211, and the solid ingredient 150 is homogenously discharged from the respective nozzles 201.

Fifth Embodiment

Figure 10:
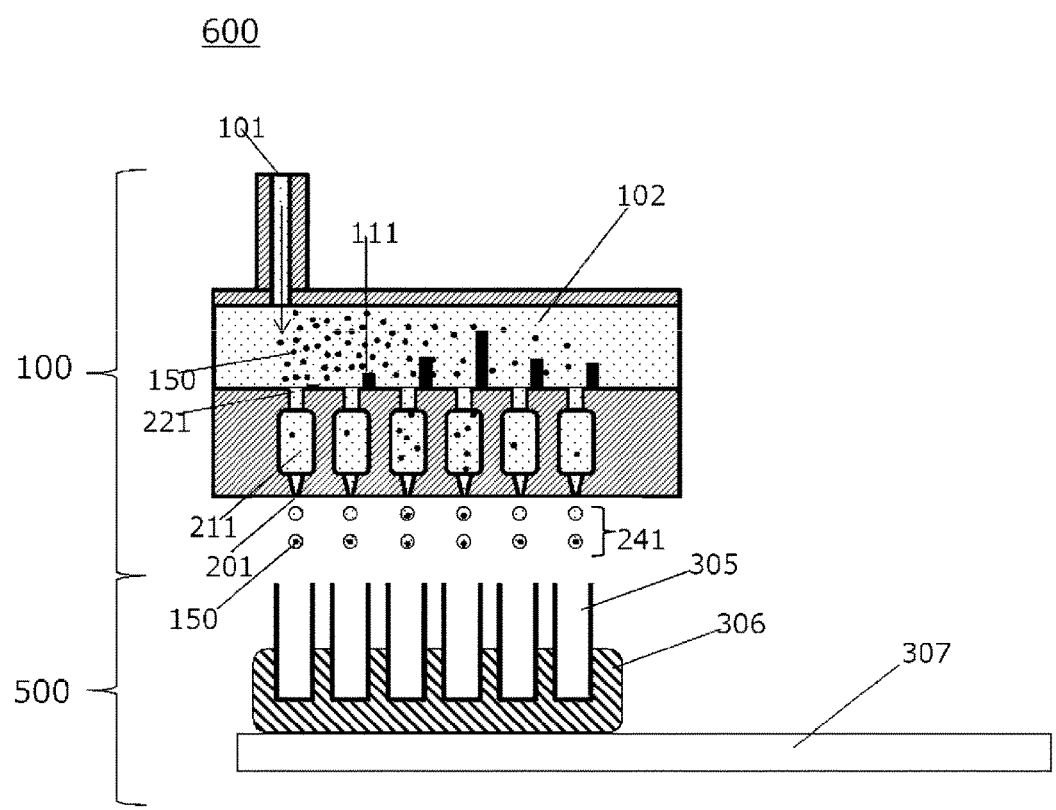
FIG. 10 is a cross-section view that shows a structure of an inkjet head according to a fifth embodiment of the disclosure.

FIG. 10 refers to an inkjet apparatus 600 in a fifth embodiment of the invention.

The inkjet apparatus 600 includes an inkjet head 100 and an object-moving mechanism 500.

The inkjet head(s) 100 is any one or more of the inkjet heads according to the above embodiments. In this example, the inkjet head according to the first embodiment is used.

The object-moving mechanism 500 includes: test tubes 305 that are objects; a test tube holder 306; and a test tube holder-moving mechanism 307.

In this apparatus, the ink is simultaneously supplied to the multiple test tubes 305. The test tubes 305 are moved by the test tube holder 306.

The inkjet head 100 may be moved. It would be sufficient that there may be a mechanism that causes relative movement between the test tube holder 306 and the inkjet head 100. However, since such a mechanism would be complex, the inkjet head 100 is preferably fixed.

Respective embodiments can be combined.

Apparatuses for coating various liquids can be realized by using the above-described inkjet heads. An object to be coated may be moved, or the inkjet head may be moved. Coating apparatuses that have a drive mechanism and a control mechanism are provided.

According to an inkjet head of the invention, it becomes possible to voluntarily control an amount of a solid ingredient included in an ink, and to introduce the solid ingredient into pressure chambers, thereby discharging the solid ingredient. Accordingly, the inkjet head can favorably be used as an inkjet head for discharging predetermined amounts of a wide variety of solid ingredients, e.g., inks including metallic materials that improves design properties, or inks including biologically functional materials such as cells.

What is claimed is:

1. An inkjet head, comprising:
multiple nozzles that each discharge droplets;
multiple pressure chambers that are each connected to the multiple nozzles, respectively, and that each generate pressures required for discharging of an ink;
a common chamber that supplies the ink to the multiple pressure chambers;
multiple discrete flow channels that each supply the ink to the respective multiple pressure chambers from the common chamber; and
an ink inlet from which the ink is supplied to the common chamber, wherein
resistant walls are provided correspondingly to respective inlets of the multiple discrete flow channels,
each of the pressure chambers is disposed in a lower portion of the respective resistance wall in a direction of gravity,
wherein the resistant walls have a triangular shape or an elliptical shape, are respectively different in height, and are located between the inlets.

2. The inkjet head according to claim 1, wherein the respective sizes of the resistant walls differ from each other.

3. The inkjet head according to claim 2, wherein the respective sizes of the resistant walls gradually become larger toward the direction from the upstream to the downstream of the flow of the ink in the common chamber.

4. The inkjet head according to claim 1, wherein the cross-section area of the common chamber gradually becomes smaller toward the direction from the upstream to the downstream of the flow of the ink in the common chamber.

5. The inkjet head according to claim 1, wherein the common chamber further includes an ink outlet from which the ink is discharged.

6. The inkjet head according to claim 1, wherein an oscillating mechanism that oscillates the ink is further provided in the common chamber.

7. The inkjet head according to claim 1, wherein the discrete flow channels are disposed in the lower part of the resistant walls in the direction of gravity, the pressure chambers are disposed in a lower portion of the discrete flow channels in the direction of gravity.

8. The inkjet head according to claim 1, wherein the common chamber, the discrete flow paths, and the pressure chambers are aligned in a direction of gravitational force.

9. The inkjet head according to claim 1, wherein a height direction of the resistant walls are the direction of gravity.

10. The inkjet head according to claim 1, wherein the resistant walls, the discrete flow channels and the pressure chamber are arranged in a direction of gravitational force in this order.

11. The inkjet head according to claim 1, wherein the ink inlet, the common chamber, the resistant walls, the discrete flow channels, the pressure chambers, and the nozzles are arranged in this order in the direction of gravity.

12. The inkjet head according to claim 1, wherein the direction in which the pressure is applied in the pressure chambers is a direction perpendicular to the direction of gravity.

13. A coating apparatus, comprising:
   the inkjet head according to claim 1;
   a holding part that holds an object; and
   a mechanism that causes relative movement between the inkjet head and the holding part.

* * * * *